United States Patent
Hoskins et al.

(12)

(10) Patent No.: US 6,271,000 B1
(45) Date of Patent: Aug. 7, 2001

(54) STREPTOCOCCUS PNEUMONIAE GENE SEQUENCE MRAY

(75) Inventors: Jo Ann Hoskins, Indianapolis; Robert Brown Peery, Brownsburg; Paul Luther Skatrud, Greenwood; Michele Louise Young Bellido, Indianapolis, all of IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 08/986,768

(22) Filed: Dec. 8, 1997

Related U.S. Application Data

(60) Provisional application No. 60/036,281, filed on Dec. 13, 1996.

(51) Int. Cl.$^7$ .................................................. C12P 21/06
(52) U.S. Cl. ..................... 435/69.3; 435/320.1; 435/69.1; 435/71.1; 435/71.2; 435/440; 435/471; 435/252.3; 435/254.11; 435/257.2; 435/822; 536/23.1; 536/23.7; 536/24.32
(58) Field of Search ................................ 435/320.1, 69.1, 435/69.3, 71.1, 440, 471, 252.3, 254.11, 257.2, 872; 536/23.1, 23.7, 24.32

(56) References Cited

PUBLICATIONS

Masato Ikeda, et al. "The *Escherichia Coli* mraY Gene Encoding UDP–N–Acetylmuramoyl–Pentapeptide: Undecaprenyl–Phosphate Phospho–N–Acetylmuramoyl–PentapeptideTransferase" *Journal of Bacteriology* 173 (3): 1021–1026 (Feb. 1991).

William L. Kelley and Costa Georgopoulos. "Positive control of the two–component RcsC/B signal transduction network by DjlA: a member of the DnaJ Family of molecular chaperones in *Escherichia coli*" *Molecular Microbiology* 25(5):913–931 (1997).

Mark. A. Lehrman. "Commentary: A family of UDP–GlcNAc/MurNAc: polyisoprenol–P GlcNAc/MurNAc–1–P transferases" *Glycobiology*4(6):768–71 (Dec. 1994).

Lindler et al. 1987. J. Bacteriol. 169(7): 3199–3208.*

Snatagene. 1991. Product Catalogue p. 292.*

Boehringer Mannheim Biochemicals 1991 Catalog. p. 557.*

Promega 1993l4 Catalog pp. 90–91.*

New England Biolabs Catalog. 1986/7 pp. 60–62.*

Laible et al. 1989. Molec. Microbiol 3(10): 1337–1348.*

Gibco Brl. 1992 Catalog p. 292.*

* cited by examiner

*Primary Examiner*—Christopher L. Chin
*Assistant Examiner*—Jennifer Graser
(74) *Attorney, Agent, or Firm*—Raymond S. Parker, III; Thomas D. Webster

(57) ABSTRACT

The invention provides isolated nucleic acid compounds encoding enzyme mraY of *Streptococcus pneumoniae*. Also provided are vectors and transformed host cells for expressing the encoded enzyme, and a method for identifying compounds that inhibit said enzyme.

12 Claims, No Drawings

SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
      (A) LENGTH: 981 base pairs
      (B) TYPE: nucleic acid
      (C) STRANDEDNESS: single
      (D) TOPOLOGY: linear (ii) MOLECULE TYPE: DNA (genomic)

(iii) HYPOTHETICAL: NO (iv) ANTI-SENSE: NO (ix) FEATURE:
      (A) NAME/KEY: CDS
      (B) LOCATION: 1..981

(xi) SEQUENCE DESCRIPTION: SEQ ID NO:1:

```
ATG TTT ATT TCC ATC AGT GCT GGA ATT GTG ACA TTT TTA CTA ACT TTA        48
Met Phe Ile Ser Ile Ser Ala Gly Ile Val Thr Phe Leu Leu Thr Leu
 1               5                  10                  15

GTA GGA ATT CCG GCC TTT ATC CAA TTT TAT AGA AAG GCG CAA ATT ACA        96
Val Gly Ile Pro Ala Phe Ile Gln Phe Tyr Arg Lys Ala Gln Ile Thr
                20                  25                  30

GGC CAG CAG ATG CAT GAG GAT GTC AAA CAG CAT CAG GCA AAA GCT GGG       144
Gly Gln Gln Met His Glu Asp Val Lys Gln His Gln Ala Lys Ala Gly
            35                  40                  45

ACT CCT ACA ATG GGA GGT TTG GTT TTC TTG ATT ACT TCT GTT TTG GTT       192
Thr Pro Thr Met Gly Gly Leu Val Phe Leu Ile Thr Ser Val Leu Val
        50                  55                  60

GCT TTC TTT TTC GCC CTA TTT AGT AGC CAA TTC AGC AAT AAT GTG GGA       240
Ala Phe Phe Phe Ala Leu Phe Ser Ser Gln Phe Ser Asn Asn Val Gly
 65                  70                  75                  80

ATG ATT TTG TTC ATC TTG GTC TTG TAT GGC TTG GTC GGA TTT TTA GAT       288
Met Ile Leu Phe Ile Leu Val Leu Tyr Gly Leu Val Gly Phe Leu Asp
                85                  90                  95

GAC TTT CTC AAG GTC TTT CGT AAA ATC AAT GAG GGG CTT AAT CCT AAG       336
Asp Phe Leu Lys Val Phe Arg Lys Ile Asn Glu Gly Leu Asn Pro Lys
                100                 105                 110
```

```
CAA AAA TTA GCT CTT CAG CTT CTA GGT GGA GTT ATC TTC TAT CTT TTC       384
Gln Lys Leu Ala Leu Gln Leu Leu Gly Gly Val Ile Phe Tyr Leu Phe
        115                 120                 125

TAT GAG CGC GGT GGC GAT ATC CTG TCT GTC TTT GGT TAT CCA GTT CAT       432
Tyr Glu Arg Gly Gly Asp Ile Leu Ser Val Phe Gly Tyr Pro Val His
130                 135                 140

TTG GGA TTT TTC TAT ATT TTC TTC GCT CTT TTC TGG CTA GTC GGT TTT       480
Leu Gly Phe Phe Tyr Ile Phe Phe Ala Leu Phe Trp Leu Val Gly Phe
145                 150                 155                 160

TCA AAC GCA GTA AAC TTG ACA GAC GGT GTT GAC GGT TTA GCT AGT ATT       528
Ser Asn Ala Val Asn Leu Thr Asp Gly Val Asp Gly Leu Ala Ser Ile
            165                 170                 175

TCC GTT GTG ATT AGT TTG TTT GCC TAT GGA GTT ATT GCC TAT GTG CAA       576
Ser Val Val Ile Ser Leu Phe Ala Tyr Gly Val Ile Ala Tyr Val Gln
            180                 185                 190

GGT CAG ATG GAT ATT CTT CTA GTG ATT CTT GCC ATG ATT GGT GGT TTG       624
Gly Gln Met Asp Ile Leu Leu Val Ile Leu Ala Met Ile Gly Gly Leu
            195                 200                 205

CTC GGT TTC TTC ATC TTT AAC CAT AAG CCT GCC AAG GTC TTT ATG GGT       672
Leu Gly Phe Phe Ile Phe Asn His Lys Pro Ala Lys Val Phe Met Gly
        210                 215                 220

GAT GTG GGA AGT TTG GCC CTA GGT GGG ATG CTG GCA GCT ATC TCT ATG       720
Asp Val Gly Ser Leu Ala Leu Gly Gly Met Leu Ala Ala Ile Ser Met
225                 230                 235                 240

GCT CTC CAC CAG GAA TGG ACT CTC TTG ATT ATC GGA ATT GTG TAT GTT       768
Ala Leu His Gln Glu Trp Thr Leu Leu Ile Ile Gly Ile Val Tyr Val
                245                 250                 255

TTT GAA ACA ACT TCT GTT ATG ATG CAA GTC AGT TAT TTC AAA CTG ACA       816
Phe Glu Thr Thr Ser Val Met Met Gln Val Ser Tyr Phe Lys Leu Thr
                260                 265                 270

GGT GGT AAA CGT ATT TTC CGT ATG ACG CCT GTA CAT CAC CAT TTT GAG       864
Gly Gly Lys Arg Ile Phe Arg Met Thr Pro Val His His His Phe Glu
        275                 280                 285

CTT GGG GGA TTG TCT GGT AAA GGA AAT CCT TGG AGC GAG TGG AAG GTT       912
Leu Gly Gly Leu Ser Gly Lys Gly Asn Pro Trp Ser Glu Trp Lys Val
        290                 295                 300

GAC TTC TTC TTT TGG GGA GTT GGG CTT CTA GCA AGT CTC CTG ACC CTC       960
Asp Phe Phe Phe Trp Gly Val Gly Leu Leu Ala Ser Leu Leu Thr Leu
305                 310                 315                 320

GCA ATT TTG TAT TTG ATG TAA                                           981
Ala Ile Leu Tyr Leu Met *
                325

(2) INFORMATION FOR SEQ ID NO:2:

(i) SEQUENCE CHARACTERISTICS:
        (A) LENGTH: 326 amino acids
        (B) TYPE: amino acid
        (D) TOPOLOGY: linear (ii) MOLECULE TYPE: protein (xi) SEQUENCE DESCRIPTION: SEQ ID NO:2:

Met Phe Ile Ser Ile Ser Ala Gly Ile Val Thr Phe Leu Leu Thr Leu
 1               5                  10                  15

Val Gly Ile Pro Ala Phe Ile Gln Phe Tyr Arg Lys Ala Gln Ile Thr
                20                  25                  30

Gly Gln Gln Met His Glu Asp Val Lys Gln His Gln Ala Lys Ala Gly
            35                  40                  45

Thr Pro Thr Met Gly Gly Leu Val Phe Leu Ile Thr Ser Val Leu Val
50                  55                  60
```

```
Ala Phe Phe Ala Leu Phe Ser Ser Gln Phe Ser Asn Asn Val Gly
 65              70                  75                  80

Met Ile Leu Phe Ile Leu Val Leu Tyr Gly Leu Val Gly Phe Leu Asp
                 85                  90                  95

Asp Phe Leu Lys Val Phe Arg Lys Ile Asn Glu Gly Leu Asn Pro Lys
                100                 105                 110

Gln Lys Leu Ala Leu Gln Leu Leu Gly Gly Val Ile Phe Tyr Leu Phe
                115                 120                 125

Tyr Glu Arg Gly Gly Asp Ile Leu Ser Val Phe Gly Tyr Pro Val His
    130                 135                 140

Leu Gly Phe Phe Tyr Ile Phe Phe Ala Leu Phe Trp Leu Val Gly Phe
145                 150                 155                 160

Ser Asn Ala Val Asn Leu Thr Asp Gly Val Asp Gly Leu Ala Ser Ile
                165                 170                 175

Ser Val Val Ile Ser Leu Phe Ala Tyr Gly Val Ile Ala Tyr Val Gln
                180                 185                 190

Gly Gln Met Asp Ile Leu Leu Val Ile Leu Ala Met Ile Gly Gly Leu
                195                 200                 205

Leu Gly Phe Phe Ile Phe Asn His Lys Pro Ala Lys Val Phe Met Gly
210                 215                 220

Asp Val Gly Ser Leu Ala Leu Gly Gly Met Leu Ala Ala Ile Ser Met
225                 230                 235                 240

Ala Leu His Gln Glu Trp Thr Leu Leu Ile Ile Gly Ile Val Tyr Val
                245                 250                 255

Phe Glu Thr Thr Ser Val Met Met Gln Val Ser Tyr Phe Lys Leu Thr
                260                 265                 270

Gly Gly Lys Arg Ile Phe Arg Met Thr Pro Val His His His Phe Glu
                275                 280                 285

Leu Gly Gly Leu Ser Gly Lys Gly Asn Pro Trp Ser Glu Trp Lys Val
                290                 295                 300

Asp Phe Phe Phe Trp Gly Val Gly Leu Leu Ala Ser Leu Leu Thr Leu
305                 310                 315                 320

Ala Ile Leu Tyr Leu Met
                325

(2) INFORMATION FOR SEQ ID NO:3:

(i) SEQUENCE CHARACTERISTICS:
        (A) LENGTH: 981 base pairs
        (B) TYPE: nucleic acid
        (C) STRANDEDNESS: single
        (D) TOPOLOGY: linear (ii) MOLECULE TYPE: mRNA (iii) HYPOTHETICAL: NO (iv) ANTI-SENSE: NO (xi) SEQUENCE DESCRIPTION: SEQ ID NO:3:

AUGUUUAUUU CCAUCAGUGC UGGAAUUGUG ACAUUUUUAC UAACUUUAGU AGGAAUUCCG      60

GCCUUUAUCC AAUUUUAUAG AAAGGCGCAA AUUACAGGCC AGCAGAUGCA UGAGGAUGUC     120

AAACAGCAUC AGGCAAAAGC UGGGACUCCU ACAAUGGGAG GUUGGUUUU CUUGAUUACU      180

UCUGUUUUGG UUGCUUUCUU UUUCGCCCUA UUUAGUAGCC AAUUCAGCAA UAAUGUGGGA     240

AUGAUUUUGU UCAUCUUGGU CUUGUAUGGC UUGGUCGGAU UUUUAGAUGA CUUUCUCAAG     300

GUCUUUCGUA AAAUCAAUGA GGGGCUUAAU CCUAAGCAAA AAUUAGCUCU UCAGCUUCUA     360
```

-continued

```
GGUGGAGUUA UCUUCUAUCU UUUCUAUGAG CGCGGUGGCG AUAUCCUGUC UGUCUUUGGU        420

UAUCCAGUUC AUUUGGGAUU UUUCUAUAUU UUCUUCGCUC UUUUCUGGCU AGUCGGUUUU        480

UCAAACGCAG UAAACUUGAC AGACGGUGUU GACGGUUUAG CUAGUAUUUC CGUUGUGAUU        540

AGUUUGUUUG CCUAUGGAGU UAUUGCCUAU GUGCAAGGUC AGAUGGAUAU UCUUCUAGUG        600

AUUCUUGCCA UGAUUGGUGG UUUGCUCGGU UUCUUCAUCU UUAACCAUAA GCCUGCCAAG        660

GUCUUUAUGG GUGAUGUGGG AAGUUUGGCC CUAGGUGGGA UGCUGGCAGC UAUCUCUAUG        720

GCUCUCCACC AGGAAUGGAC UCUCUUGAUU AUCGGAAUUG UGUAUGUUUU UGAAACAACU        780

UCUGUUAUGA UGCAAGUCAG UUAUUUCAAA CUGACAGGUG GUAAACGUAU UUUCCGUAUG        840

ACGCCUGUAC AUCACCAUUU UGAGCUUGGG GGAUUGUCUG GUAAAGGAAA UCCUUGGAGC        900

GAGUGGAAGG UUGACUUCUU CUUUUGGGGA GUUGGGCUUC UAGCAAGUCU CCUGACCCUC        960

GCAAUUUUGU AUUUGAUGUA A                                                 981
```

(2) INFORMATION FOR SEQ ID NO:4:

(i) SEQUENCE CHARACTERISTICS:
        (A) LENGTH: 3190 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:4:

```
CGTCAGTGCT AAAACAGGGG AAATTCTGGC AACAACGCAA CGACCGACCT TTGATGCAGA         60

TACAAAAGAA GGCATTACAG AGGACTTTTT TGGCGTGATA TCCTTTACCA AAGTAACTAT        120

GAGCCAGGTT CCACTATGAA AGTGATGATG TTGGCTGCTG CTATTGATAA AATACCTTT         180

CCAGGAGGAG AAGTCTTTAA TAGTAGTGAG TTAAAAATTG CAGATGCCAC GATTCGAGAT        240

TGGGACGTTA ATGAAGGATT GACTGGTGGC AGAATGATGT CTTTTTCTCA AGGTTTTGCA        300

CACTCAAGTA ACGTTGGGAT GACCCTCCTT GAGCAAAAGA TGGGAGATGC TACCTGGCTT        360

GATTATCTTA ATCGTTTTAA ATTTGGTGTT CCGACCCGTT TCGGTTTGAC GGATGAGTAT        420

GCTGGTCAGC TTCCTGCGGA TAATATTGTC AACATTGCGC AAAGCTCATT TGGACAAGGG        480

ATTTCAGTGA CCCAGACGCA AATGATTCGT GCCTTTACAG CTATTGCTAA TGACGGTGTC        540

ATGCTGGAGC CTAAATTTAT TAGTGCCATT TATGATCCAA ATGATCAAAC TGCTCGGAAA        600

TCTCAAAAAG AAATTGTGGG AAATCCTGTT TCTAAAGATG CAGCTAGTCT AACTCGGACT        660

AACATGGTTT TGGTAGGGAC GGATCCGGTT TATGGAACCA TGTATAACCA CAGCACAGGC        720

AAGCCAACTG TAACTGTTCC TGGGCAAAAT GTAGCCCTCA AGTCTGGTAC GGCTCAGATT        780

GCTGACGAGA AAAATGGTGG TTATCTAGTC GGGTTAACCG ACTATATTTT CTCGGCTGTT        840

CGATGAGTCC GGCTGAAAAT CCTGGATTTT ATCTTGTATG TGACGGTCCA ACAACCTGGA        900

ACATTATTCA GGTATTCAGT TGGGAGAATT TGCCAATCCT ATCTTGGAGC GGGCTTCAGC        960

TATGAAAGAC TCTCTCAATC TTCAAACAAC AGCTAAGGCT TTGGAGCAAG TAAGTCAACA       1020

AAGTCCTTAT CCTATGCCCA GTGTCAAGGA TATTTCACCT GGTGATTTAG CAGAAGAATT       1080

GCGTCGCAAT CTTGTACAAC CCATCGTTGT GGGAACAGGA ACGAAGATTA AAACAGTTC        1140
```

-continued

```
TGCTGAAGAA GGGAAGAATC TTGCCCCGAA CCAGCAAGTC CTTATCTTAT CTGATAAAGC    1200

AGAGGAGGTT CCAGATATGT ATGGTTGGAC AAAGGAGACT GCTGAGACCC TTGCTAAGTG    1260

GCTCAATATA GAACTTGAAT TTCAAGGCTC GGGCTCTACT GTGCAGAAGC AAGATGTTCG    1320

TGCTAACACA GCTATCAAGG ACATTAAAAA AATTACATTA ACTTTAGGAG ACTAATATGT    1380

TTATTTCCAT CAGTGCTGGA ATTGTGACAT TTTTACTAAC TTTAGTAGGA ATTCCGGCCT    1440

TTATCCAATT TTATAGAAAG GCGCAAATTA CAGGCCAGCA GATGCATGAG GATGTCAAAC    1500

AGCATCAGGC AAAAGCTGGG ATTCCTACAA TGGGAGGTTT GGTTTTCTTG ATTACTTCTG    1560

TTTTGGTTGC TTTCTTTTTC GCCCTATTTA GTAGCCAATT CAGCAATAAT GTGGGAATGA    1620

TTTTGTTCAT CTTGGTCTTG TATGGCTTGG TCGGATTTTT AGATGACTTT CTCAAGGTCT    1680

TTCGTAAAAT CAATGAGGGG CTTAATCCTA AGCAAAAATT AGCTCTTCAG CTTCTAGGTG    1740

GAGTTATCTT CTATCTTTTC TATGAGCGCG GTGGCGATAT CCTGTCTGTC TTTGGTTATC    1800

CAGTTCATTT GGGATTTTTC TATATTTTCT TCGCTCTTTT CTGGCTAGTC GGTTTTTCAA    1860

ACGCAGTAAA CTTGACAGAC GGTGTTGTAC GGTTTAGCTA GTATTTCCGT TGTGATTAGT    1920

TTGTTTGCCT ATGGAGTTAT TGCCTATGTG CAAGGTCAGA TGGATATTCT TCTAGTGATT    1980

CTTGCCATGA TTGGTGGTTT GCTCGGTTTC TTCATCTTTA ACCATAAGCC TGCCAAGGTC    2040

TTTATGGGTG ATGTGGGAAG TTTGGCCCTA GGTGGGATGC TGGCAGCTAT CTCTATGGCT    2100

CTCCACCAGG AATGGACTCT CTTGATTATC GGAATTGTGT ATGTTTTTGA AACAACTTCT    2160

GTTATGATGC AAGTCAGTTA TTTCAAACTG ACAGGTGGTA AACGTATTTT CCGTATGACG    2220

CCTGTACATC ACCATTTTGA GCTTGGGGGA TTGTCTGGTA AAGGAAATCC TTGGAGCGAG    2280

TGGAAGGTTG ACTTCTTCTT TTGGGGAGTT GGGCTTCTAG CAAGTCTCCT GACCCTCGCA    2340

ATTTTGTATT TGATGTAAGA ATGGCACCCT GATGTTTCAG GGTGTTTTTG TGTTTAAATA    2400

CACAATGAAA ATCAAAGAAC AAACTAGAAA GCTAACTTTA GGCTGCTCAA AATATAATAT    2460

ATTGAAACTA GAATAGTACA CCTCTACTTC TAAAACATTG TTAGAAATCG ATTTGACTGT    2520

CCTGAACGAT TTATCCTGTT CTTATTTCAT TTTACTATAC AGTTTCGAGG TTGTAGATAA    2580

GGCGAAGCTG ATGTGGTTTG AAGAGATTTT CTGAAAAGTG TTAACACCTA CAGACAAGCC    2640

TGACGATAGC AAGAACTACC CTACTCGATA GGTATCGGCT TTTGCTTTCT GAAAAAAATT    2700

ATTTTAAGCA TTTGACAAAT CTAGCAACAA AAAATTCTAT AAATATAATA GATTGAAACT    2760

AGAATAGTAC ACATCTACTT CTAAAACATT GTTAGAAATC GATTTGACTG TCCTGATCGA    2820

TTTGTCCTGT TCTTGTTTCA TTTTACTATA TTTCTATGAT AAAACGCATA GTATCAAGTT    2880

TTCTTAATCC CCTGATACTA TGCGTGTTTG TAATTTTTAA GATTTTGTGC TTAGAGTCGA    2940

CTCCTTATTT TAGATATTTA AAAGGAATCT CACTTCCACA GAGCCAGTTG TAGACTTGGT    3000

CATTAACAAA TACATTCATG GCTTCGTGAG CATACTCAGG CATGATACGA TAGGTTTTAT    3060

CGCAGGTCAG ACGATTATAA ATCGCAAACT GGGTAATGGG ATAGCAAACA TCGTCGTCCA    3120

AGCCCGTAAT CATCTTAACC TCACCTTGGA TACGATGGGC AAGATTTTTG ACATCGACTC    3180

TAGAGGATCC                                                          3190
```

STREPTOCOCCUS PNEUMONIAE GENE SEQUENCE MRAY

This application claims the benefit of U.S. Provisional Application No. 60/036,281, filed Dec. 13, 1996.

BACKGROUND OF THE INVENTION

This invention provides isolated DNA sequences, proteins encoded thereby, and methods of using said DNA and protein in a variety of applications.

Widespread antibiotic resistance in common pathogenic bacterial species has justifiably alarmed the medical and research communities. Frequently, resistant organisms are co-resistant to several antibacterial agents. Penicillin resistance in *Streptococcus pneumoniae* has been particularly problematic. This organism causes upper respiratory tract infections. Modification of a penicillin-binding protein (PBP) underlies resistance to penicillin in the majority of cases. Combating resistance to antibiotic agents will require research into the molecular biology of pathogenic organisms. The goal of such research will be to identify new antibacterial agents.

While researchers continue to develop antibiotics effective against a number of microorganisms, *Streptococcus pneumoniae* has been more refractory. In part, this is because Streptococcus pneumoniae is highly recombinogenic and readily takes up exogenous DNA from its surroundings. Thus, there is a need for new antibacterial compounds and new targets for antibacterial therapy in *Streptococcus pneumoniae*.

BRIEF SUMMARY OF THE INVENTION

The present invention relates to an isolated gene and encoded protein from *S. pneumoniae*. The invention enables: (1) preparation of probes and primers for use in hybridizations and PCR amplifications, (2) production of proteins and RNAs encoded by said gene and related nucleic acids, and (3) methods to identify compounds that bind and/or inhibit said protein(s).

In one embodiment the present invention relates to an isolated nucleic acid molecule encoding an mraY protein.

In another embodiment, the invention relates to a nucleic acid molecule comprising the nucleotide sequence identified as SEQ ID NO:1, SEQ ID NO:3, or SEQ ID NO:4.

In another embodiment, the present invention relates to a nucleic acid that encodes SEQ ID NO:2.

In another embodiment the present invention relates to an isolated protein molecule, wherein said protein molecule comprises the sequence identified as SEQ ID NO:2.

In yet another embodiment, the present invention relates to a recombinant DNA vector that incorporates the mraY gene in operable linkage to gene expression sequences enabling the gene to be transcribed and translated in a host cell.

In still another embodiment the present invention relates to host cells that have been transformed or transfected with the cloned mraY gene such that said gene is expressed in the host cell.

This invention also provides a method of determining whether a nucleic acid sequence of the present invention, or fragment thereof, is present in a sample, comprising contacting the sample, under suitable hybridization conditions, with a nucleic acid probe of the present invention.

In a still further embodiment, the present invention relates to a method for identifying compounds that bind and/or inhibit the mraY protein.

DETAILED DESCRIPTION OF THE INVENTION

"ORF" (i.e. "open reading frame") designates a region of genomic DNA beginning with a Met or other initiation codon and terminating with a translation stop codon, that potentially encodes a protein product. "Partial ORF" means a portion of an ORF as disclosed herein such that the initiation codon, the stop codon, or both are not disclosed. "Consensus sequence" refers to an amino acid or nucleotide sequence that may suggest the biological function of a protein, DNA, or RNA molecule. Consensus sequences are identified by comparing proteins, RNAs, and gene homologues from different species.

The terms "cleavage" or "restriction" of DNA refers to the catalytic cleavage of the DNA with a restriction enzyme that acts only at certain sequences in the DNA (viz. sequence-specific endonucleases). The various restriction enzymes used herein are commercially available and their reaction conditions, cofactors, and other requirements are used in the manner well known to one of ordinary skill in the art. Appropriate buffers and substrate amounts for particular restriction enzymes are specified by the manufacturer or can readily be found in the literature. "Essential genes" or "essential ORFs" or "essential proteins" refer to genomic information or the protein(s) or RNAs encoded thereby, that when disrupted by knockout mutation, or by other mutation, result in a loss of viability of cells harboring said mutation. "Non-essential genes" or "non-essential ORFs" or "non-essential proteins" refer to genomic information or the protein(s) or RNAs encoded therefrom which when disrupted by knockout mutation, or other mutation, do not result in a loss of viability of cells harboring said mutation. "Minimal gene set" refers to a genus comprising about 256 genes conserved among different bacteria such as *M. genitalium* and *H. influenzae*. The minimal gene set may be necessary and sufficient to sustain life. See e.g. A. Mushegian and E. Koonin, "A minimal gene set for cellular life derived by comparison of complete bacterial genomes" Proc. Nat. Acad. Sci. 93, 10268–273 (1996). "Knockout mutant" or "knockout mutation" as used herein refers to an in vitro engineered disruption of a region of native chromosomal DNA, typically within a protein coding region, such that a foreign piece of DNA is inserted within the native sequence. A knockout mutation occurring in a protein coding region prevents expression of the wild-type protein. This usually leads to loss of the function provided by the protein. A "knockout cassette" refers to a fragment of native chromosomal DNA having cloned therein a foreign piece of DNA that may provide a selectable marker.

The term "plasmid" refers to an extrachromosomal genetic element. The starting plasmids herein are either commercially available, publicly available on an unrestricted basis, or can be constructed from available plasmids in accordance with published procedures. In addition, equivalent plasmids to those described are known in the art and will be apparent to the ordinarily skilled artisan.

"Recombinant DNA cloning vector" as used herein refers to any autonomously replicating agent, including, but not limited to, plasmids and phages, comprising a DNA molecule to which one or more additional DNA segments can or have been added.

The term "recombinant DNA expression vector" as used herein refers to any recombinant DNA cloning vector, for example a plasmid or phage, in which a promoter and other regulatory elements are present to enable transcription of the inserted DNA.

The term "vector" as used herein refers to a nucleic acid compound used for introducing exogenous DNA into host cells. A vector comprises a nucleotide sequence which may encode one or more protein molecules. Plasmids, cosmids, viruses, and bacteriophages, in the natural state or which have undergone recombinant engineering, are examples of commonly used vectors.

The terms "complementary" or "complementarity" as used herein refer to the capacity of purine and pyrimidine nucleotides to associate through hydrogen bonding to form double stranded nucleic acid molecules. The following base pairs are related by complementarity: guanine and cytosine; adenine and thymine; and adenine and uracil. As used herein, "complementary" applies to all base pairs comprising two single-stranded nucleic acid molecules. "Partially complementary" means one of two single-stranded nucleic acid molecules is shorter than the other, such that one of the molecules remains partially single-stranded.

"Oligonucleotide" refers to a short nucleotide chain comprising from about 2 to about 25 nucleotides.

"Isolated nucleic acid compound" refers to any RNA or DNA sequence, however constructed or synthesized, which is locationally distinct from its natural location.

A "primer" is a nucleic acid fragment which functions as an initiating substrate for enzymatic or synthetic elongation of, for example, a nucleic acid molecule.

The term "promoter" refers to a DNA sequence which directs transcription of DNA to RNA.

A "probe" as used herein is a labeled nucleic acid compound which can be used to hybridize with another nucleic acid compound.

The term "hybridization" or "hybridize" as used herein refers to the process by which a single-stranded nucleic acid molecule joins with a complementary strand through nucleotide base pairing.

"Substantially purified" as used herein means a specific isolated nucleic acid or protein, or fragment thereof, in which substantially all contaminants (i.e. substances that differ from said specific molecule) have been separated from said nucleic acid or protein. For example, a protein may, but not necessarily, be "substantially purified" by the IMAC method as described herein.

"Selective hybridization" refers to hybridization under conditions of high stringency. The degree of hybridization between nucleic acid molecules depends upon, for example, the degree of complementarity, the stringency of hybridization, and the length of hybridizing strands.

The term "stringency" relates to nucleic acid hybridization conditions. High stringency conditions disfavor non-homologous base pairing. Low stringency conditions have the opposite effect. Stringency may be altered, for example, by changes in temperature and salt concentration. Typical high stringency conditions comprise hybridizing at 50° C. to 65° C. in 5×SSPE and 50% formamide, and washing at 50° C. to 65° C. in 0.5×SSPE; typical low stringency conditions comprise hybridizing at 35° C. to 37° C. in 5×SSPE and 40% to 45% formamide and washing at 42° C. in 1×–2×SSPE.

"SSPE" denotes a hybridization and wash solution comprising sodium chloride, sodium phosphate, and EDTA, at pH 7.4. A 20× solution of SSPE is made by dissolving 174 g of NaCl, 27.6 g of NaH2PO4.H2O, and 7.4 g of EDTA in 800 ml of H2O. The pH is adjusted with NaOH and the volume brought to 1 liter.

"SSC" denotes a hybridization and wash solution comprising sodium chloride and sodium citrate at pH 7. A 20×solution of SSC is made by dissolving 175 g of NaCl and 88 g of sodium citrate in 800 ml of H2O. The volume is brought to 1 liter after adjusting the pH with 10N NaOH.

DETAILED DESCRIPTION OF THE INVENTION

The mraY gene disclosed herein (SEQ ID NO:1) and related nucleic acids, for example, SEQ ID NO:3 and SEQ ID NO:4, encode the enzyme phospho-MurNAc-pentapeptide translocase (hereinafter "translocase"), which couples UDPMurNAc-pentapeptide to undecaprenyl phosphate to give undecaprenyl diphospho-MurNAcpentapeptide and UMP. The translocase enzyme comprises one step in bacterial cell wall biosynthesis. This enzyme can be used in a screen for agents that bind and/or inhibit the activity thereof, as a lead to new antibacterial agents.

In one embodiment, the proteins of this invention are purified and used to screen for compounds that bind and/or inhibit the activity of said proteins. A variety of suitable screens are contemplated. For example, the protein(s) can be labeled by known techniques, such as radiolabeling or fluorescent tagging, or labeling with biotin/avidin. Thereafter, binding of a test compound to a labeled protein can be determined by any suitable means, well known to the skilled artisan.

Skilled artisans will recognize that the DNA molecules of this invention, or fragments thereof, can be generated by general cloning methods. PCR amplification using oligonucleotide primers targeted to any suitable region of SEQ ID NO:1 is preferred. Methods for PCR amplification are widely known in the art. See e.g. PCR Protocols: A Guide to Method and Application, Ed. M. Innis et al., Academic Press (1990) or U.S. Pat. No. 4,889,818, which hereby is incorporated by reference. A PCR comprises DNA, suitable enzymes, primers, and buffers, and is conveniently carried out in a DNA Thermal Cycler (Perkin Elmer Cetus, Norwalk, Conn.). A positive PCR result is determined by, for example, detecting an appropriately-sized DNA fragment following agarose gel electrophoresis.

The DNAs of the present invention may also be produced using synthetic methods well known in the art. (See, e.g., E. L. Brown, R. Belagaje, M. J. Ryan, and H. G. Khorana, Methods in Enzymology, 68:109–151 (1979)). An apparatus such as the Applied Biosystems Model 380A or 380B DNA synthesizers (Applied Biosystems, Inc., 850 Lincoln Center Drive, Foster City, Calif. 94404) may be used to synthesize DNA. Synthetic methods rely upon phosphotriester chemistry [See, e.g., M. J. Gait, ed., Oligonucleotide Synthesis, A Practical Approach, (1984)], or phosphoramidite chemistry.

Protein Production Methods

The present invention relates further to substantially purified proteins encoded by the gene disclosed herein.

Skilled artisans will recognize that proteins can be synthesized by different methods, for example, chemical methods or recombinant methods, as described in U.S. Pat. No. 4,617,149, which hereby is incorporated by reference.

The principles of solid phase chemical synthesis of polypeptides are well known in the art and may be found in general texts relating to this area. See, e.g., H. Dugas and C. Penney, Bioorganic Chemistry (1981) Springer-Verlag, New York, 54–92. Peptides may be synthesized by solid-phase methodology utilizing an Applied Biosystems 430A peptide synthesizer (Applied Biosystems, Foster City, Calif.) and synthesis cycles supplied by Applied Biosystems. Protected amino acids, such as t-butoxycarbonyl-protected amino acids, and other reagents are commercially available from many chemical supply houses.

The proteins of the present invention can also be made by recombinant DNA methods. Recombinant methods are preferred if a high yield is desired. Recombinant methods involve expressing the cloned gene in a suitable host cell. The gene is introduced into the host cell by any suitable means, well known to those skilled in the art. While chromosomal integration of the cloned gene is within the scope of the present invention, it is preferred that the cloned gene be maintained extra-chromosomally, as part of a vector in which the gene is in operable-linkage to a promoter.

Recombinant methods can also be used to overproduce a membrane-bound or membrane-associated protein. In some cases, membranes prepared from recombinant cells expressing such proteins provide an enriched source of the protein.

Expressing Recombinant Proteins in Procaryotic and Eucaryotic Host Cells

Procaryotes are generally used for cloning DNA sequences and for constructing vectors. For example, the Escherichia coli K12 strain 294 (ATCC No. 31446) is particularly useful for expression of foreign proteins. Other strains of *E. coli*, bacilli such as *Bacillus subtilis*, enterobacteriaceae such as *Salmonella typhimurium* or *Serratia marcescans*, various Pseudomonas species may also be employed as host cells in cloning and expressing the recombinant proteins of this invention. Also contemplated are various strains of Streptococcus and Streptocmyces.

For effective recombinant protein production, a gene must be linked to a promoter sequence. Suitable bacterial promoters include b -lactamase [e.g. vector pGX2907, ATCC 39344, contains a replicon and b -lactamase gene], lactose systems [Chang et al., Nature (London), 275:615 (1978); Goeddel et al., Nature (London), 281:544 (1979)], alkaline phosphatase, and the tryptophan (trp) promoter system [vector pATH1 (ATCC 37695)] designed for the expression of a trpE fusion protein. Hybrid promoters such as the tac promoter (isolatable from plasmid pDR540, ATCC-37282) are also suitable. Promoters for use in bacterial systems also will contain a Shine-Dalgarno sequence, operably linked to the DNA encoding the desired polypeptides. These examples are illustrative rather than limiting.

A variety of mammalian cells and yeasts are also suitable hosts. The yeast *Saccharomyces cerevisiae* is commonly used. Other yeasts, such as *Kluyveromyces lactis*, are also suitable. For expression of recombinant genes in Saccharomyces, the plasmid YRp7 (ATCC-40053), for example, may be used. See, e.g., L. Stinchcomb, et al., Nature, 282:39 (1979); J. Kingsman et al., Gene, 7:141 (1979); S. Tschemper et al., Gene, 10:157 (1980). Plasmid YRp7 contains the TRP1 gene, a selectable marker for a trpl mutant.

Purification of Recombinantly-Produced Protein

An expression vector carrying a nucleic acid or gene of the present invention is transformed or transfected into a suitable host cell using standard methods. Cells that contain the vector are propagated under conditions suitable for expression of a recombinant protein. For example, if the gene is under the control of an inducible promoter, then suitable growth conditions would incorporate the appropriate inducer. The recombinantly-produced protein may be purified from cellular extracts of transformed cells by any suitable means.

In a preferred process for protein purification a gene is modified at the 5' end, or at some other position, such that the encoded protein incorporates several histidine residues (viz. "histidine tag"). This "histidine tag" enables "immobilized metal ion affinity chromatography" (IMAC), a single-step protein purification method described in U.S. Pat. No. 4,569,794, which hereby is incorporated by reference. The IMAC method enables isolation of substantially pure protein starting from a crude cellular extract.

As skilled artisans will recognize, owing to the degeneracy of the code, the proteins of the invention can be encoded by a large genus of different nucleic acid sequences. This invention further comprises said genus.

The ribonucleic acid compounds of the invention may be prepared using the polynucleotide synthetic methods discussed supra, or they may be prepared enzymatically using RNA polymerase to transcribe a DNA template.

The most preferred systems for preparing the ribonucleic acids of the present invention employ the RNA polymerase from the bacteriophage T7 or the bacteriophage SP6. These RNA polymerases are highly specific, requiring the insertion of bacteriophage-specific sequences at the 5' end of a template. See, J. Sambrook, et al., supra, at 18.82–18.84.

This invention also provides nucleic acids that are complementary to the sequences disclosed herein.

The present invention also provides probes and primers, useful for a variety of molecular biology techniques including, for example, hybridization screens of genomic or subgenomic libraries, or detection and quantification of mRNA species as a means to analyze gene expression. A nucleic acid compound is provided comprising any of the sequences disclosed herein, or a complementary sequence thereof, or a fragment thereof, which is at least 15 base pairs in length, and which will hybridize selectively to *Streptococcus pneumoniae* DNA or mRNA. Preferably, the 15 or more base pair compound is DNA. A probe or primer length of at least 15 base pairs is dictated by theoretical and practical considerations. See e.g. B. Wallace and G. Miyada, "Oligonucleotide Probes for the Screening of Recombinant DNA Libraries," In Methods in Enzymology, Vol. 152, 432–442, Academic Press (1987).

The probes and primers of this invention can be prepared by methods well known to those skilled in the art (See e.g. Sambrook et al. supra). In a preferred embodiment the probes and primers are synthesized by the polymerase chain reaction (PCR).

The present invention also relates to recombinant DNA cloning vectors and expression vectors comprising the nucleic acids of the present invention. Preferred nucleic acid vectors are those that comprise DNA. The skilled artisan understands that choosing the most appropriate cloning vector or expression vector depends on the availability of restriction sites, the type of host cell into which the vector is to be transfected or transformed, the purpose of transfection or transformation (e.g., stable transformation as an extrachromosomal element, or integration into a host chromosome), the presence or absence of readily assayable or selectable markers (e.g., antibiotic resistance and metabolic markers of one type and another), and the number of gene copies desired in the host cell.

Suitable vectors comprise RNA viruses, DNA viruses, lytic bacteriophages, lysogenic bacteriophages, stable bacteriophages, plasmids, viroids, and the like. The most preferred vectors are plasmids.

Host cells harboring the nucleic acids disclosed herein are also provided by the present invention. A preferred host is *E. coli* transfected or transformed with a vector comprising a nucleic acid of the present invention.

The invention also provides a host cell capable of expressing a gene described herein, said method comprising transforming or otherwise introducing into a host cell a recombinant DNA vector comprising an isolated DNA sequence that encodes said gene. The preferred host cell is any strain of *E. coli* that can accommodate high level expression of an exogenously-introduced gene. Transformed host cells are cultured under conditions well known to skilled artisans, such that said gene is expressed, thereby producing the encoded protein in the recombinant host cell.

To discover compounds having antibacterial activity, one can look for agents that inhibit cell growth and/or viability by, for example, inhibiting enzymes required for cell wall biosynthesis, and/or by identifying agents that interact with membrane proteins. A method for identifying such compounds comprises contacting a suitable protein or membrane preparation with a test compound and monitoring by any suitable means an interaction and/or inhibition of a protein of this invention.

For example, the instant invention provides a screen for compounds that interact with the proteins of the invention, said screen comprising:

a) preparing a protein, or membranes enriched in a protein;

b) exposing the protein or membranes to a test compound; and c) detecting an interaction or inhibition of a protein with said compound, by any suitable means.

The screening method of this invention may be adapted to automated procedures such as a PANDEX® (Baxter-Dade Diagnostics) system, allowing for efficient high-volume screening of compounds.

In a typical screen, a protein of the invention is prepared as described herein, preferably using recombinant DNA technology. A test compound is introduced into a reaction vessel containing said protein. The reaction/interaction of said protein and said compound is monitored by any suitable means. In a preferred method, a radioactively-labeled or chemically-labeled compound or protein is used. A specific association between the test compound and protein is monitored by any suitable means.

In such a screening protocol MraY is prepared as described herein, preferably using recombinant DNA technology. A test compound is introduced into a reaction vessel containing the MraY protein or fragment thereof. Binding of MraY by a test compound is determined by any suitable means. For example, in one method radioactively-labeled or chemically-labeled test compound may be used. Binding of the protein by the compound is assessed, for example, by quantifying bound label versus unbound label using any suitable method. Binding of a test compound may also be carried out by a method disclosed in U.S. Pat. No. 5,585,277, which hereby is incorporated by reference. In this method, binding of a test compound to a protein is assessed by monitoring the ratio of folded protein to unfolded protein, for example by monitoring sensitivity of said protein to a protease, or amenability to binding of said protein by a specific antibody against the folded state of the protein.

The foregoing screening methods are useful for identifying a ligand of a MraY protein, perhaps as a lead to a pharmaceutical compound for modulating the state of differentiation of an appropriate tissue. A ligand that binds MraY, or related fragment thereof, is identified, for example, by combining a test ligand with MraY under conditions that cause the protein to exist in a ratio of folded to unfolded states. If the test ligand binds the folded state of the protein, the relative amount of folded protein will be higher than in the case of a test ligand that does not bind the protein. The ratio of protein in the folded versus unfolded state is easily determinable by, for example, susceptibility to digestion by a protease, or binding to a specific antibody, or binding to chaperonin protein, or binding to any suitable surface.

The following examples more fully describe the present invention. Those skilled in the art will recognize that the particular reagents, equipment, and procedures described are merely illustrative and are not intended to limit the present invention in any manner.

EXAMPLE 1

Production of a Vector for Expressing *S. pneumoniae* mraY in a Host Cell

An expression vector suitable for expressing *S. pneumoniae* mraY in a variety of procaryotic host cells, such as *E. coli*, is easily made. The vector contains an origin of replication (Ori), an ampicillin resistance gene (Amp) useful for selecting cells which have incorporated the vector following a tranformation procedure, and further comprises the T7 promoter and T7 terminator sequences in operable linkage to the mraY coding region. Plasmid pET11A (obtained from Novogen, Madison, Wis.) is a suitable parent plasmid. pET11A is linearized by restriction with endonucleases NdeI and BamHI. Linearized pET11A is ligated to a DNA fragment bearing NdeI and BamHI sticky ends and comprising the coding region of the *S. pneumoniae* mraY (SEQ ID NO:1). The coding region for mraY is easily produced by PCR technology using suitably designed primers to the ends of the coding region specified in SEQ ID NO:1.

The mraY gene used in this construct is slightly modified at the 5' end (amino terminus of encoded protein) in order to simplify purification of the encoded protein product. For this purpose, an oligonucleotide encoding 8 histidine residues is inserted after the ATG start codon. Placement of the histidine residues at the amino terminus of the encoded protein serves to enable the IMAC one-step protein purification procedure.

EXAMPLE 2

Recombinant Expression and Purification of a Protein Encoded by *S. pneumoniae* mraY Gene An expression vector that carries the mraY gene from *S. pneumoniae* as disclosed herein and which is operably-linked to an expression promoter is transformed into *E. coli* BL21 (DE3)(hsdS gal lcIts857 ind1Sam7nin5lacUV5-T7gene 1) using standard methods (see Example 1). Transformants, selected for resistance to ampicillin, are chosen at random and tested for the presence of the vector by agarose gel electrophoresis using quick plasmid preparations. Colonies which contain the vector are grown in L broth and the protein product encoded by the vector-borne ORF is purified by immobilized metal ion affinity chromatography (IMAC), essentially as described in U.S. Pat. No. 4,569,794.

Briefly, the IMAC column is prepared as follows. A metal-free chelating resin (e.g. Sepharose 6B IDA, Pharmacia) is washed in distilled water to remove preservative substances and infused with a suitable metal ion [e.g. Ni(II), Co(II), or Cu(II)] by adding a 50 mM metal chloride or metal sulfate aqueous solution until about 75% of the interstitial spaces of the resin are saturated with colored metal ion. The column is then ready to receive a crude cellular extract containing the recombinant protein product.

After removing unbound proteins and other materials by washing the column with any suitable buffer, pH 7.5, the bound protein is eluted in any suitable buffer at pH 4.3, or preferably with an imidizole-containing buffer at pH 7.5.

EXAMPLE 3

Biochemical Assay for Inhibitors of *Streptococcus pneumoniae* mraY Enzyme

The activity of the mraY enzyme is assayed by monitoring the coupling of substrates UDPMurNAc-pentapeptide and undecaprenyl phosphate. Substrates for peptidoglycan synthesis are prepared from *S. pneumoniae* membranes using standard methods (See e.g. Mengin-Lecreulx et al. J. Bacteriol. 173, 4625–4636, 1991; or H. Tanaka et.al. Biochem. Biophys. Res. Comm. 86, 902–908, 1979). Briefly, the reaction contains in a final volume of 30 ul, 0.25M Tris-HCl, pH 8.5, 25 mM MgC12, 1 mM DTT, 10 ul of membrane particulate fraction (~200 ug protein), and 3.3×10−4 M UDP-MurNAc-L-Ala-D-Glu-[3H]-meso-Dpm-D-Ala-D-Ala (11.6 uCi/umol). The labeled membrane particulae fraction is prepared as described by Oka (Antimicrob. Ag. Chemother. 10, 579–591, 1976). The reaction is incubated at 25° C. for 10–60 minutes. After incubation, the reaction is stopped by adding 15 ul of 6M pyridinium acetate, pH 4.2. The lipid products are extracted twice with n-butanol, transferred to a scintillation vial, dried, and the radioactivity estimated by counting using a toluene based scintillation fluid. Alternatively, samples are placed in a boiling water bath for 2 minutes and applied to Whatman 3MM filter paper. The filter is subjected to descending chromatography for 16 hours in isobutyric acid-1M NH40H (5:3 vol/vol). Areas corresponding to peptidoglycan, UDP-MurNAc-pentapeptide, and lipid intermediates are cut out and assayed by scintillation counting.

Inhibition studies are carried out using the reaction conditions described in the preceding paragraph. Test inhibitory compounds are added to a final concentration of between 1 mM and 10 mM, and the percentage inhibition ascertained by comparison with a control in which no test inhibitor is present.

We claim:

1. An isolated nucleic acid compound encoding the protein of SEQ ID NO:2.

2. An isolated nucleic acid compound, wherein the sequence of said compound is selected from the group consisting of:

(a) SEQ ID NO:1;
(b) SEQ ID NO:3; and
(c) a nucleic acid compound filly complementary to (a) or (b).

3. An isolated nucleic acid compound, wherein the sequence of said compound is SEQ ID NO:4.

4. An isolated nucleic acid compound of claim 2 wherein the sequence of said compound is SEQ ID NO:1 or a sequence fully complementary to SEQ ID NO:1.

5. An isolated nucleic acid compound of claim 2 wherein the sequence of said compound is SEQ ID NO:3 or a sequence fully complementary to SEQ ID NO:3.

6. An isolated nucleic acid compound that hybridizes to SEQ ID NO:1 under high stringency conditions.

7. A vector comprising an isolated nucleic acid compound of claim 2.

8. A vector, as in claim 7, wherein said isolated nucleic acid compound is SEQ ID NO:1, operably-linked to a promoter sequence.

9. A host cell containing a vector of claim 7.

10. A host cell containing a vector of claim 8.

11. A method for constructing a recombinant host cell that expresses SEQ ID NO:2, said method comprising introducing into said host cell by any suitable means a vector of claim 8.

12. A method for expressing SEQ ID NO:2 in the recombinant host cell of claim 11, said method comprising culturing said recombinant host cell under conditions suitable for gene expression.

* * * * *